(12) United States Patent
Doherty

(10) Patent No.: US 11,021,325 B2
(45) Date of Patent: Jun. 1, 2021

(54) RESCUE DEVICE

(71) Applicant: Sebastien Doherty, Pointe-Claire (CA)

(72) Inventor: Sebastien Doherty, Pointe-Claire (CA)

(*) Notice: Subject to any disclaimer, the term of this patent is extended or adjusted under 35 U.S.C. 154(b) by 134 days.

(21) Appl. No.: 16/270,795

(22) Filed: Feb. 8, 2019

(65) Prior Publication Data
US 2019/0283967 A1     Sep. 19, 2019

(30) Foreign Application Priority Data

Mar. 14, 2018 (GB) .................................. 1804037

(51) Int. Cl.
| B65G 7/12 | (2006.01) |
| A62B 3/00 | (2006.01) |
| A61F 5/37 | (2006.01) |

(52) U.S. Cl.
CPC .............. B65G 7/12 (2013.01); A61F 5/3738 (2013.01); A62B 3/00 (2013.01)

(58) Field of Classification Search
CPC .. A62B 1/16; A62B 3/00; A62B 35/04; A62B 1/20; A62B 35/0043; A63B 29/02; A63B 21/0557; A63B 21/00043; A63B 21/0552; A61F 5/3776; A61F 5/26; A61F 5/3738; B65G 7/12; B66C 1/18; D07B 1/18
USPC .................................... 294/140; D8/394, 356
See application file for complete search history.

(56) References Cited

U.S. PATENT DOCUMENTS

| 2,224,103 | A | * | 12/1940 | Nilson | A63B 21/00185 482/124 |
|---|---|---|---|---|---|
| 2,407,714 | A | | 9/1946 | Maloney | |
| 3,275,205 | A | | 9/1966 | Howd et al. | |
| 4,765,279 | A | | 8/1988 | Klickstein | |
| 5,101,768 | A | | 4/1992 | Cates | |
| D362,327 | S | | 9/1995 | Nelson | |
| D429,386 | S | | 8/2000 | Tingler | |
| 6,205,584 | B1 | | 3/2001 | Yocco | |
| D482,837 | S | | 11/2003 | Westbrook | |
| 6,641,008 | B2 | | 11/2003 | Falzone et al. | |
| 6,671,899 | B1 | | 1/2004 | Oja | |
| 7,000,809 | B1 | * | 2/2006 | Stroud | A45F 5/02 224/250 |
| 7,818,818 | B2 | | 10/2010 | Grilliot et al. | |
| 7,963,365 | B2 | | 6/2011 | Grilliot et al. | |
| 8,002,082 | B2 | | 8/2011 | Snedeker | |

(Continued)

FOREIGN PATENT DOCUMENTS

| CA | 2276084 | 12/1999 |
| CN | 201179288 | 1/2009 |

(Continued)

*Primary Examiner* — Daniel J Colilla

(57) ABSTRACT

A rescue device comprising a closed loop element made of a flexible material and first and second slidable elements mounted to the closed loop element so as to be slidable therealong while frictionally engaging the closed loop element. The first and second slidable elements each pinch the closed loop element against itself to define a pair of opposed end loop portions and an intermediate loop portion extending therebetween, the intermediate loop portion extending between the first and second slidable elements and each of the end loop portions extending from a respective one of the first and second slidable elements opposed to the intermediate loop portion.

20 Claims, 3 Drawing Sheets

(56) References Cited

U.S. PATENT DOCUMENTS

| | | | |
|---|---|---|---|
| 8,016,335 B2 | 9/2011 | McKay | |
| D665,963 S | 8/2012 | Liljedahl | |
| D719,303 S | 12/2014 | Anderson | |
| 8,905,451 B1 | 12/2014 | Golz | |
| 10,603,528 B1 * | 3/2020 | Bologna | A62B 35/0006 |
| 2006/0070800 A1 | 4/2006 | Lewis et al. | |
| 2007/0169246 A1 | 7/2007 | Sloan et al. | |
| 2008/0245610 A1 | 10/2008 | Lee | |
| 2008/0256680 A1 | 10/2008 | Peksoz et al. | |
| 2014/0102458 A1 * | 4/2014 | Landow | A61D 7/04 |
| | | | 128/207.11 |

FOREIGN PATENT DOCUMENTS

| | | |
|---|---|---|
| GB | 1198175 | 7/1970 |
| WO | 2004085240 | 10/2004 |

* cited by examiner

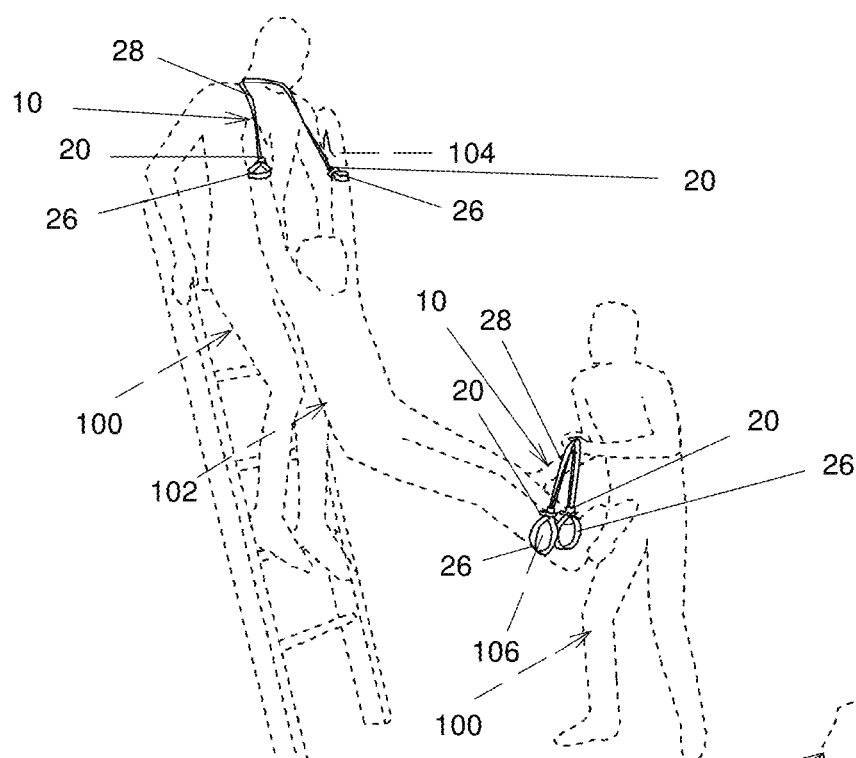
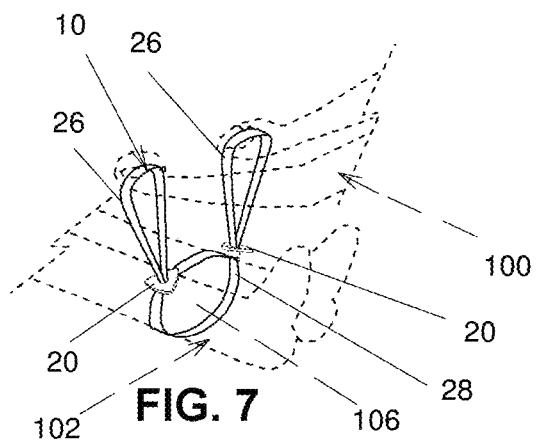
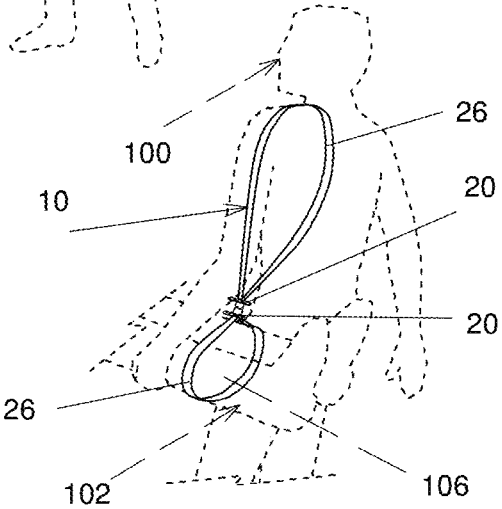
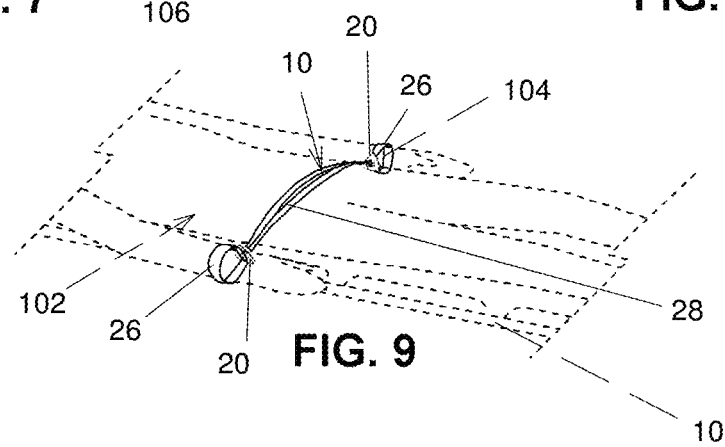

RESCUE DEVICE

FIELD OF THE INVENTION

The present invention relates to the general field of portable rescue equipment, and is more specifically concerned with a rescue device.

BACKGROUND

In rescue operations, there is a need sometimes to quickly move a victim away from a danger zone. Hand carrying the victim can be difficult and requires great muscular strength and endurance. This can even be almost impossible in some situations.

Against this background, there exists a need in the industry to provide a rescue device. An object of the present invention is therefore to provide such a rescue device.

SUMMARY OF THE INVENTION

In a broad aspect, there is provided a rescue device including a closed loop element made of a flexible material; and first and second slidable elements mounted to the closed loop element so as to be slidable therealong while frictionally engaging the closed loop element. The first and second slidable elements each pinch the closed loop element against itself to define a pair of opposed end loop portions and an intermediate loop portion extending therebetween, the intermediate loop portion extending between the first and second slidable elements and each of the end loop portions extending from a respective one of the first and second slidable elements opposed to the intermediate loop portion.

There may also be provided a rescue device wherein the first and second slidable elements each include a tube defining a passageway extending axially therethrough, the closed loop element being mounted in the passageway.

There may also be provided a rescue device wherein the closed loop element defines a pair of thicker portions thicker than adjacent portions of the closed loop element, each of the thicker portions being provided in a respective one of the end loop portions, the closed loop element being too thick in the thicker portions to be insertable through the passageway.

There may also be provided a rescue device wherein the closed loop element includes two bands of material each defining a pair of opposed band end portions, the bands of material being secured to each other at the band end portions, the bands of material overlapping each other in the band end portion to define the thicker portions.

There may also be provided a rescue device wherein the bands of material are stitched to each other in the band end portions.

There may also be provided a rescue device wherein the bands of material are each provided with a patch of miniature hook and loop material at each of their band end portions, the patches of miniature hook and loop material being complementary to each other to allow attachment of the bands of material to form the closed loop element.

There may also be provided a rescue device wherein the bands of material are substantially rectangular.

There may also be provided a rescue device wherein the bands of material are made of fabric.

There may also be provided a rescue device wherein the bands of material are substantially parallel to each other in the passageway.

There may also be provided a rescue device wherein the bands of material are wider than the passageway.

There may also be provided a rescue device wherein the passageway is provided with an inside screw thread extending axially along at least a portion thereof.

There may also be provided a rescue device wherein the passageway is substantially cylindrical.

There may also be provided a rescue device wherein the first and second slidable elements each define a respective flange extending substantially radially outwardly from the tube.

There may also be provided a rescue device wherein the flange has a generally triangular configuration.

In another broad aspect, there is provided a method of using the rescue device in the rescue of a human having first and second limbs, a torso and a neck, the method comprising: inserting the first limb in a first one of the end loop portions which is adjacent the first slidable element; and moving the first slidable element along the closed loop element to shorten the first one of the end loop portions to secure the rescue device to the first limb.

There may also be provided a method further comprising inserting the second limb in a second one of the end loop portions which is adjacent the second slidable element; moving the second slidable element along the closed loop element to shorten the second one of the end loop portions to secure the rescue device to the second limb; and using the intermediate loop portion to handle the human through the first and second limbs.

There may also be provided a method wherein the first and second limbs are arms.

There may also be provided a method wherein the first and second limbs are legs.

There may also be provided a method further comprising inserting the second limb in a second one of the end loop portions which is adjacent the second slidable element; and moving the second slidable element along the closed loop element to shorten the second one of the end loop portions to secure the rescue device to the second limb; the first and second limbs being arms; the method further comprising, with the human in a supine or prone position, laying the intermediate loop portion on the hip so that the arms are supported thereby through the rescue device.

There may also be provided a method wherein the first limb is an arm, the method further comprising passing a second one of the end loop portions around the neck to form a sling supporting the arm.

In yet another broad aspect, there is provided a method of using the rescue device in the rescue of a human having a pair of legs, the method comprising: inserting the legs in a selected loop portion selected from the end loop portions and the intermediate loop portion; moving at least one of the first and second slidable elements along the closed loop element to shorten the selected loop portion; and using another loop portion selected from the end loop portions and the intermediate loop portion and differing from the selected loop portion to handle the human.

Advantageously, the rescue device of the present invention comprises a relatively small number of components and, thus, is relatively simple and economical to manufacture, and does not get easily tangled up. Furthermore, in some embodiments, the rescue device of the present invention is relatively easily and quickly put to use, even in freezing weather conditions with hands wearing winter gloves. Still furthermore, the rescue device of the present invention provides a relatively high versatility in terms of practical ways and configurations it can be used in the general field of rescue operations.

The present application claims priority from UK Request for a Patent 1804037.8 filed Mar. 14, 2018, the contents of which is hereby incorporated by reference in its entirety.

Other objects, advantages and features of the present invention will become more apparent upon reading of the following non-restrictive description of some embodiments thereof, given by way of example only with reference to the accompanying drawings.

BRIEF DESCRIPTION OF THE DRAWINGS

FIG. 6, in an environmental view, illustrates two rescue personnel each using the rescue device of FIG. 1 for carrying a victim down a ladder;

FIG. 7, in an environmental view, illustrates the rescue device of FIG. 1 engaged in a first configuration around the ankles of a victim for carrying by a rescue personnel;

FIG. 8, in an environmental view, illustrates the rescue device of FIG. 1 engaged in a second configuration around the ankles of a victim and a shoulder of a rescue personnel;

FIG. 9, in an environmental view, illustrates the rescue device of FIG. 1 used for securing the hands of an unconscious victim laying on a stretcher;

DETAILED DESCRIPTION

The term "substantially" is used throughout this document to indicate variations in the thus qualified terms. These variations are variations that do not materially affect the manner in which the device described herein works and can be due, for example, to uncertainty in manufacturing processes or to small deviations from a nominal value or ideal shape that do not cause significant changes to the invention. These variations are to be interpreted from the point of view of the person skilled in the art.

Figure 1:
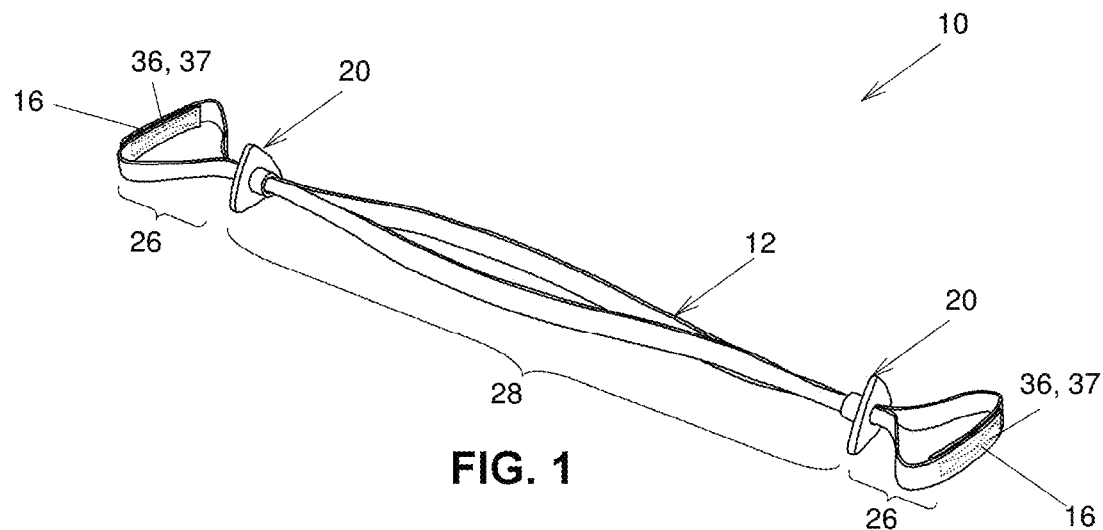
FIG. 1, in a perspective view, illustrates an embodiment of a rescue device in accordance with the invention.

Referring to FIG. 1 there is shown a rescue device 10 in accordance with an embodiment of the present invention. The rescue device 10 includes a closed loop element 12 formed of a substantially flexible material. In some embodiments, the closed loop element 12 is a topologically homeomorphic to a torus. That is, it forms a single loop delimiting a single aperture without being attached to itself anywhere in the aperture. When stretched between two opposite end portions 16 thereof, the closed loop element 12 forms a substantially elongated looped double strap having a predetermined length.

Figure 2:
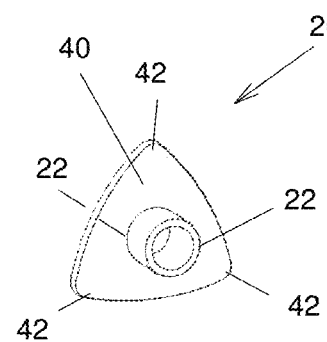
FIG. 2, in a perspective view, illustrates a slidable element, part of the rescue device of FIG. 1.
Figure 3:
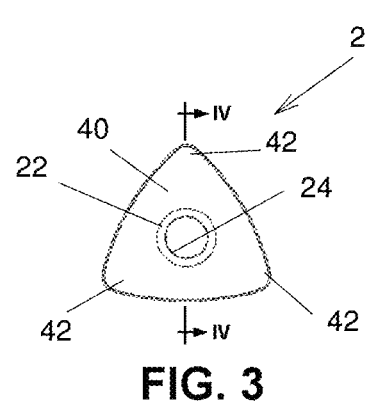
FIG. 3, in an end elevational view, illustrates the slidable element of FIG. 2.
Figure 4:
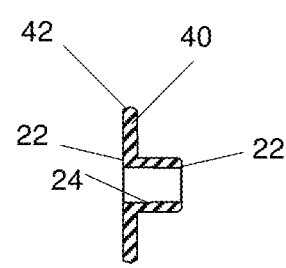
FIG. 4, in a cross-sectional view taken along section line IV-IV of FIG. 3, illustrates the slidable element of FIG. 2.

The rescue device 10 further includes a pair of slidable elements 20 mounted to the closed loop element 12 so as to be slidable therealong while frictionally engaging the closed loop element 12. Referring collectively to FIGS. 2 to 3, each one in the pair of slidable elements 20 defines opposed longitudinal end portions 22 that are spaced apart a distance that is typically much shorter than the predetermined length of the closed loop element 12, and defines a tubular passageway 24 extending through the slidable element 20 axially between the end portions 22. Furthermore, each one in the pair of slidable elements 20 has its tubular passageway 24 coaxially engaged around a portion of the closed loop element 12.

In some embodiments, the tubular passageway 24 has predetermined passageway diameter and passageway length that are suitably sized and shaped for impinging a sufficient friction force on its respective length portion of the closed loop element 12 for allowing each slidable element 20 to substantially self-maintain its position therealong. Yet, the impinged friction force is small enough to allow a user to manually move with one hand, and without using excessive force, each slidable element 20 in a user selected direction along the closed loop element 12 while the other hand retains a portion thereof adjacent the opposite end portion 22 of the slidable element 20, relative to the user selected direction.

Thus, as seen in FIG. 1, the first and second slidable elements 20 each pinch the closed loop element 12 against itself to define a pair of opposed end loop portions 26 and an intermediate loop portion 28 extending therebetween. The intermediate loop portion 28 extends between the slidable elements 20 and each of the end loop portions 26 extending from a respective one of the slidable elements 20 opposed to the intermediate loop portion 28. The length of the end loop portions 26, and therefore of the intermediate loop portion 28, is selectively adjustable by sliding the slidable elements 20 along the closed loop element 12.

Hence, for example and as illustrated in FIG. 6, each one in the pair of end loop portions 26 may be engaged and have its dimension substantially rapidly shortened and secured, by sliding the slidable element 20, around a respective limb of a patient, for example one in a pair of arms or wrists 104, legs or ankles 106 or other limb portions of a victim 102, with the intermediate loop portion 28 usable as a handle means for dragging, lifting or carrying the victim.

Alternatively, as illustrated in FIG. 9, the pair of end loop portions 26 may be used as a means for securing the wrists 104 of, for example, an unconscious victim 102, from falling off the sides of a stretcher 108 or the like. Thus, in this configuration, with the victim 102 in a supine or prone position, the loop intermediate portion is laid on the hip so that the arms are supported thereby through the rescue device 10.

Furthermore, as illustrated in FIG. 7, the rescue device 10 may alternatively allow a user 100 to selectively engage a pair of wrists, ankles 106, as illustrated, or other limb portions together in the intermediate loop portion 28 and use both end loop portions 26 as gripping loops.

Furthermore, as illustrated in FIG. 8, the rescue device 10 may alternatively allow a user 100 to selectively engage a pair of wrists, ankles or limb portions together in one end loop portion 26 and use the other end loop portion 26 as a shoulder strap for ease of carrying a victim 102.

Figure 10:
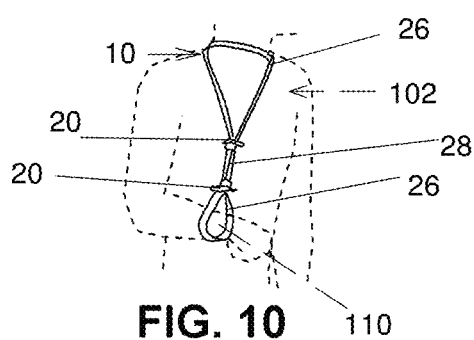
FIG. 10, in an environmental view, illustrates the rescue device of FIG. 1 used as an arm sling.

Furthermore, as illustrated in FIG. 10, the rescue device 10 may alternatively allow a user to use it as an arm sling with one end loop portion 26 engaged around the neck and the other end loop portion 26 engaged around a wrist or forearm of a patient or victim 102.

Figure 5:
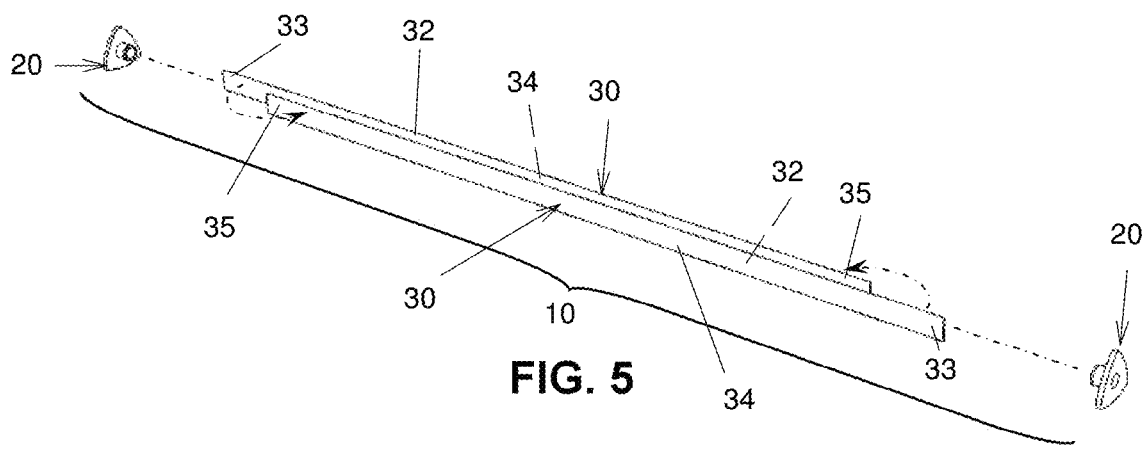
FIG. 5, in a perspective disassembled view, illustrates the rescue device of FIG. 1.

In some embodiments, as illustrated in FIG. 5, the closed loop element 12 includes a pair of bands of materials 30, having for example substantially similar lengths. Each one in the pair of bands of materials 30 has an inner surface 32 and an outer surface 34. Furthermore, each one in the pair of bands of materials 30 has an end portion 33 of its inner surface 32 that overlaps and is attached to corresponding and oppositely facing end portion 35 of the outer surface 34 of the other one in the pair of bands of materials 30, thus forming the closed loop element 12, as seen in FIG. 1. The overlapping portions thus attached to one another cooperatively form a bulge that prevents the slidable elements 20 from being pushed off an end of the closed loop element 12. Thus, the closed loop element 12 defines a pair of thicker portions 37 thicker than adjacent portions of the closed loop element 12, each of the thicker portions 37 being provided in a respective one of the end loop portions 26. The closed loop element 12 is too thick in the thicker portions 37 to be insertable through the passageway 24.

In some embodiments, the overlapping and oppositely facing inner and outer surfaces 32 and 34 are fixedly attached to one another through stitches 36 as illustrated in FIG. 1.

As exemplified in FIG. 5, a relatively simple and economical method of assembling the rescue device 10 may be represented by the following steps. In a first step, positioning the bands of material 30 in a substantially parallel configuration. In a second step, engaging the tubular passageway 24 of each slidable element 20 through one or at each end of the parallel configuration and along a respective portion thereof. In a third step, suitably stitching together the overlapping end portions of the inner and outer surfaces 32 and 34.

Figure 13:
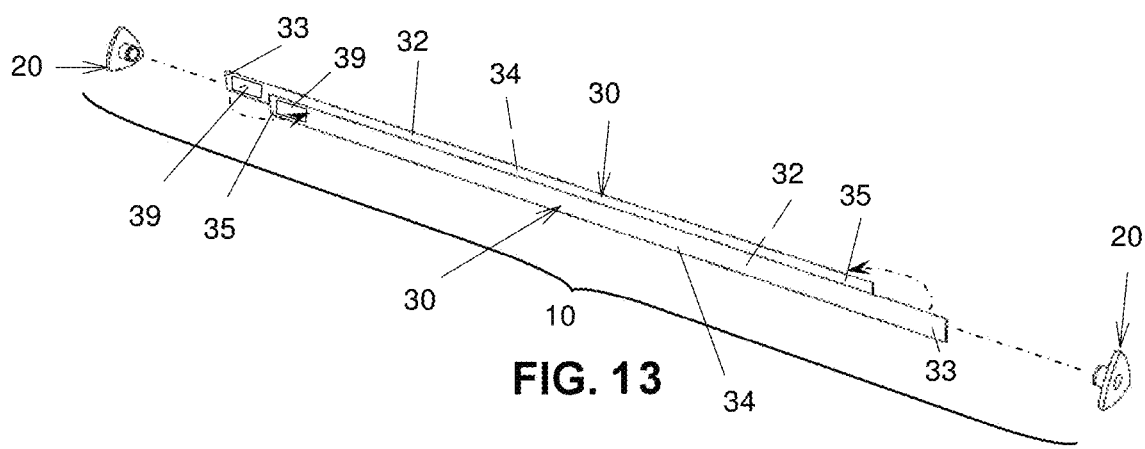
FIG. 13, in a perspective disassembled view, illustrates an alternative embodiment of a rescue device.

In some other embodiments, as seen in FIG. 13, the overlapping and oppositely facing end portions 33 and 35 are removably attached to one another through compatible pairs of Velcro® elements attached to each other. In other words, in such embodiments, patches of miniature hook and loop material 39 are provided at each band end portions of the bands of materials 30. It should be noted that the patches of miniature hook and loop material 39 are hidden from view in FIG. 13 at one of the ends of the bands of materials 30. The patches of miniature hook and loop material 39 are complementary to each other to allow attachment of the bands of material 30 to form the closed loop element 12. Thus, an end loop portion 26 may be engaged around a limb or torso portion of a victim 102 without having first to engage the latter through the free end thereof, which is not always possible in certain emergency situations.

In some embodiments, as best illustrated in FIGS. 2 and 3, at least one in the pair of slidable elements 20 includes a flange 40 protruding radially outwardly from one end portion 22 thereof relative to the tubular passageway 24. Typically, the flange 40 protrudes radially outwardly from each slidable element 20 at an end portion 22 thereof that is adjacent a respective one of the end loop portions 26, as best illustrated in FIG. 1. In some embodiments, the flange 40 defines at least one angular peripheral portion 42 for ease of rotating the at least one slidable element 20 coaxially around the closed loop element 20. In other words, in such embodiments, the flange 40 is not disc-shaped. As exemplified in FIGS. 2 and 3, the flange 40 may have a substantially triangular configuration defining three relatively smooth angular peripheral portions 42.

In some embodiments, the predetermined length of the closed loop element 12 is between 20 and 80 inches (between 50.8 and 203.2 cm) and the closed loop element 12 has a width of between ½ inch and 2 inches (between 1.3 and 5 cm). For example, the predetermined length of the closed loop element 12 is roughly 46 inches (116.8 cm) and the width of the closed loop element 12 is roughly ¾ of an inch (1.9 cm). Furthermore, in some embodiments, the end portions of the inner and outer surfaces 32 and 34 of each bands of materials 30 overlap one another a length of between 1 and 6 inches (between 2.5 and 15.2 cm), for example roughly 3 inches (7.6 cm), thus conveniently providing a relatively comfortable hand grip portion along a periphery of each one of the end loop portions 26.

In some embodiments, the tubular passageway 24 of each one in the pair of slidable elements 20 has a substantially rounded cross-section and is therefore substantially cylindrical. Furthermore, in some embodiments, each one in the pair of slidable elements 20 has a passageway length of between 0.5 and two 2 inches (between 1.3 and 5 cm), and a passageway diameter of between 0.5 inch and 1.5 inches (between 1.3 and 3.8 cm). For example, the passageway length is roughly 1.5 inches (3.8 cm) and the passageway diameter is roughly ½ inch (1.3 cm).

In some embodiments, the closed loop element 12 is made of fabric, for example a non-stretchable and weather resistant webbing material such as nylon or a material, or combination of materials having equivalent characteristics. The bands of materials 30 are also typically substantially rectangular, although other shapes are within the scope of the invention.

In some embodiments, each one in the pair of slidable elements 20 is made of a resilient polymeric material that maintains at least minimal resiliency characteristics in freezing weather conditions. Thus, the slidable elements 20 may remain substantially movable along the closed loop element even though the hands of the user 100 are protected with winter gloves, which are generally not reputed to provide a firm grip on small objects in such conditions.

Figure 11:
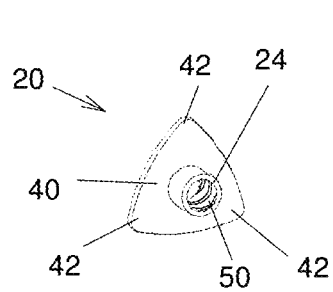
FIG. 11, in a perspective view, illustrates a second embodiment of a slidable element usable in the rescue device of FIG. 1.

In an alternate embodiment, as illustrated in FIG. 11, each one in the pair of slidable elements 20 further defines inwardly protruding screw thread configurations 50 extending axially along at least part of the inner surface portions of the tubular passageway 24.

Figure 12:
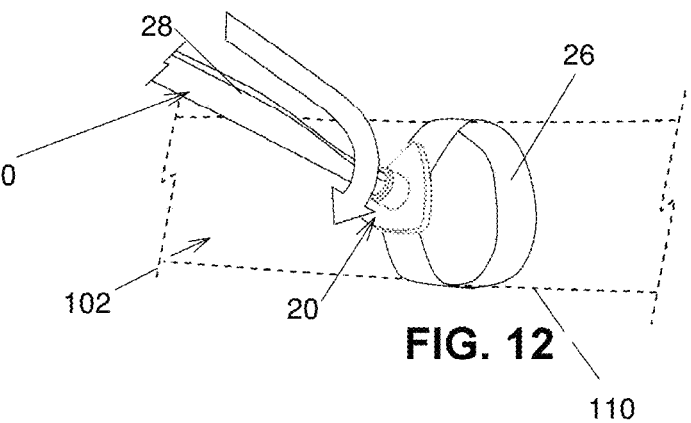
FIG. 12, in an environmental view, illustrates the slidable element of FIG. 11, here shown being sled along a looped doubled strap portion of the rescue device of FIG. 1 for threadedly tightening a loop end portion thereof engaged around a limb portion of a victim.

The screw thread configurations 50 are suitably sized and shaped for allowing a user to threadedly impinge a significant gripping and securing friction between the slidable element 20 and the closed loop element 12 by suitably rotating the slidable element 20 as the latter is pushed toward a respective end loop portion 26 engaged around a limb portion 110 of a victim 102, as illustrated in FIG. 12.

In some embodiments (not shown in the drawings), the rescue device 10 further includes a pair of auxiliary Velcro® elements. Each one in the pair of auxiliary Velcro® elements is attached along a surface portion of a respective one of the overlapping portions of the bands of materials 30 that is facing distally away from the rescue device 10. The rescue device 10 further includes a pair of compatible Velcro® elements to the auxiliary Velcro® elements that are fixedly attached in a spaced apart relationship along surface portions of garments worn by rescue personnel, removably attaching therebetween the rescue device 10.

For example (not shown in the drawings), the pair of compatible Velcro® elements may be attached in a spaced apart relationship on each side of a centred lower front edge portion of a coat worn by a rescue personnel so as to removably attach the rescue device 10 thereon, with its closed loop element 12 extending substantially around the rear lower edge portion of the coat.

In some embodiments, the bands of material 30 are wider than the passageway 24 when unfolded. Thus, the bands of material 30 are folded in the passageway 24 about a generally longitudinally extending fold line. They are also generally parallel to each other in the passageway 24. This configuration may improve the frictional characteristics between the closed loop element 12 and the slidable elements 20.

Although the present invention has been described hereinabove by way of exemplary embodiments thereof, it will be readily appreciated that many modifications are possible in the exemplary embodiments without materially departing from the novel teachings and advantages of this invention. Accordingly, the scope of the claims should not be limited by the exemplary embodiments, but should be given the broadest interpretation consistent with the description as a whole. The present invention can thus be modified without departing from the spirit and nature of the subject invention as defined in the appended claims.

What is claimed is:

1. A rescue device comprising:
   a closed loop element made of a flexible material; and
   first and second slidable elements mounted to the closed loop element so as to be slidable therealong while frictionally engaging the closed loop element, the first and second slidable elements each including a tube defining a passageway extending axially therethrough, the closed loop element being mounted in the passageway, at least one of the passageways being provided with an inside screw thread extending axially along at least a portion thereof;
   wherein the first and second slidable elements each pinch the closed loop element against itself to define a pair of opposed end loop portions and an intermediate loop portion extending therebetween, the intermediate loop portion extending between the first and second slidable elements and each of the end loop portions extending from a respective one of the first and second slidable elements opposed to the intermediate loop portion.

2. The rescue device as defined in claim 1, wherein the closed loop element defines a pair of thicker portions thicker than adjacent portions of the closed loop element, each of the thicker portions being provided in a respective one of the end loop portions, the closed loop element being too thick in the thicker portions to be insertable through at least one of the passageways.

3. The rescue device as defined in claim 2, wherein the closed loop element includes two bands of material each defining a pair of opposed band end portions, the bands of material being secured to each other at the band end portions, the bands of material overlapping each other in the band end portion to define the thicker portions.

4. The rescue device as defined in claim 3, wherein the bands of material are stitched to each other in the band end portions.

5. The rescue device as defined in claim 3, wherein the bands of material are each provided with a patch of miniature hook and loop material at each of their band end portions, the patches of miniature hook and loop material being complementary to each other to allow attachment of the bands of material to form the closed loop element.

6. The rescue device as defined in claim 3, wherein the bands of material are substantially rectangular.

7. The rescue device as defined in claim 3, wherein the bands of material are made of fabric.

8. The rescue device as defined in claim 3, wherein the bands of material are substantially parallel to each other in each passageway.

9. The rescue device as defined in claim 3, wherein the bands of material are wider than each passageway.

10. The rescue device as defined in claim 1, wherein the at least one of the passageways is substantially cylindrical.

11. The rescue device as defined in claim 1, wherein the first and second slidable elements each define a respective flange extending substantially radially outwardly from the tube.

12. The rescue device as defined in claim 11, wherein at least one of the flanges has a generally triangular configuration.

13. A method of using the rescue device of claim 1 in the rescue of a human having first and second limbs, a hip and a neck, the method comprising:
    inserting the first limb in a first one of the end loop portions which is adjacent the first slidable element; and
    moving the first slidable element along the closed loop element to shorten the first one of the end loop portions to secure the rescue device to the first limb.

14. The method as defined in claim 13, further comprising inserting the second limb in a second one of the end loop portions which is adjacent the second slidable element; and
    moving the second slidable element along the closed loop element to shorten the second one of the end loop portions to secure the rescue device to the second limb;
    the first and second limbs being arms;
    the method further comprising, with the human in a supine or prone position, laying the intermediate loop portion on the human at the hip so that the arms are supported thereby through the rescue device.

15. The method as defined in claim 13, wherein the first limb is an arm, the method further comprising passing a second one of the end loop portions around the neck to form a sling supporting the arm.

16. The method as defined in claim 13, further comprising inserting the second limb in a second one of the end loop portions which is adjacent the second slidable element;
    moving the second slidable element along the closed loop element to shorten the second one of the end loop portions to secure the rescue device to the second limb; and
    using the intermediate loop portion to handle the human through the first and second limbs.

17. The method as defined in claim 16, wherein the first and second limbs are arms.

18. The method as defined in claim 16, wherein the first and second limbs are legs.

19. A method of using the rescue device of claim 1 in the rescue of a human having a pair of legs, the method comprising:
    inserting the legs in a selected loop portion selected from the end loop portions and the intermediate loop portion;
    moving at least one of the first and second slidable elements along the closed loop element to shorten the selected loop portion; and
    using an other loop portion selected from the end loop portions and the intermediate loop portion and differing from the selected loop portion to handle the human.

20. A rescue device comprising:
    a closed loop element made of a flexible material; and first and second slidable elements mounted to the closed loop element so as to be slidable therealong while frictionally engaging the closed loop element, the first and second slidable elements each including a tube defining a passageway extending axially therethrough, the closed loop element being mounted in the passageway, the closed loop element defining a pair of thicker portions thicker than adjacent portions of the closed loop element, each of the thicker portions being provided in a respective one of the end loop portions, the closed loop element being too thick in the thicker portions to be insertable through at least one of the passageways;

wherein the closed loop element includes two bands of material each defining a pair of opposed band end portions, the bands of material being secured to each other at the band end portions, the bands of material overlapping each other in the band end portion to define the thicker portions and the bands of material being stitched to each other in the band end portions; and wherein the first and second slidable elements each pinch the closed loop element against itself to define a pair of opposed end loop portions and an intermediate loop portion extending therebetween, the intermediate loop portion extending between the first and second slidable elements and each of the end loop portions extending from a respective one of the first and second slidable elements opposed to the intermediate loop portion.

* * * * *